United States Patent [19]

Hughes

[11] 4,294,992

[45] Oct. 13, 1981

[54] PROCESS FOR THE PRODUCTION OF ALKYL ARYL ETHERS

[75] Inventor: Graham K. Hughes, Hackettstown, N.J.

[73] Assignee: The Southland Corporation, Dallas, Tex.

[21] Appl. No.: 114,601

[22] Filed: Jan. 23, 1980

[51] Int. Cl.³ .......................................... C07C 43/205
[52] U.S. Cl. ................................. 568/632; 568/630
[58] Field of Search ............................. 568/630, 632

[56] References Cited

U.S. PATENT DOCUMENTS 2,264,371  12/1941  Harvey ................................. 568/630

FOREIGN PATENT DOCUMENTS 646736  11/1950  United Kingdom ................ 568/630

Primary Examiner—Paul J. Killos
Attorney, Agent, or Firm—Cushman, Darby & Cushman

[57] ABSTRACT

Alkyl aryl ethers are produced by incrementally reacting an acid and an alkanol with a phenol and continuously removing water formed as a by-product of the reaction. Preferably, the acid is sulfuric acid; the alkanol is methanol; and the phenol is $\beta$-naphthol. The process is carried out at an elevated temperature, preferably at a temperature ranging from 125° to 175° C.

8 Claims, No Drawings

PROCESS FOR THE PRODUCTION OF ALKYL ARYL ETHERS

This invention relates to the preparation of alkyl aryl ethers and, more particularly, to the production of lower alkyl naphthalene ethers and, especially, to the production of 2-methoxy naphthalenes, for use in steroid manufacture and perfumery.

BACKGROUND OF THE INVENTION

Heretofore, the production of alkyl aryl ethers involved reacting a phenol with either a dialkyl sulfate or an alkyl halide (Wagner and Zook, Synthetic Organic Chemistry, Chapter 6, pp. 226–229, Wiley, 1953). This same type general reaction scheme has also been employed to produce β-methoxy naphthalene in a 73% yield, by reacting dimethyl sulfate with β-naphthol (Krum and Waldo, JACS 1921, 43, 2223).

Further, the reaction of alcohols with a phenol has been disclosed by Stork in JACS 1947, 69, 576–9, this reaction involving mixing methanol, β-naphthol and extremely large amounts of sulfuric acid together, and boiling the mixture for a period of time, the resulting product being obtained in a yield of about 85%.

GENERAL DESCRIPTION OF THE INVENTION

It has now been found that alkyl aryl ethers can be rapidly and economically prepared with a quantitative conversion of the phenol initial reactant by incrementally reacting an acid and an alkanol with a phenol, and continuously removing water formed as a by-product of said reaction. The reaction is generally carried out at an elevated temperature.

DETAILED DESCRIPTION OF THE INVENTION

The present invention, more particularly, relates to the production of 2-alkoxy arylene by incrementally reacting a mixture of an acid, such as an organic or inorganic acid, and an alkanol with a phenol. The acid is, preferably, an inorganic acid such as sulfuric acid, although other acids such as phosphoric acid, hydrochloric acid and p-toluene sulfonic acid can also be employed.

The alkanol is, preferably methanol, but other lower alkanols such as ethanol, propanol and butanol can also be used.

Preferably, also, the acid and alkanol are introduced into the reaction zone in the form of a mixture.

The phenol is, preferably, β-naphthol although other hydroxy containing condensed aromatic ring system compounds can be employed. For instance, α-naphthol can also be used.

The rate of addition of the mixture of inorganic acid and lower alkanol to the β-naphthol ranges between about 0.133–0.907 weight percent per minute based on the β-naphthol charge. The volume ratio of inorganic acid to lower alkanol in said mixture ranges from about 0.1 to 0.7:1 based on the lower alkanol while the mole ratio of lower alkanol to β-naphthol generally ranges from about 2 to 12:1. Generally, an excess of lower alkanol is employed.

The mixture of lower alkanol and inorganic acid is sparged into molten β-naphthol while concurrently permitting water of reaction to distill out through a condenser to a receiver. A certain amount of lower alkanol passes straight through without reaction, thus aiding in the removal of water formed by the reaction between β-naphthol and the remainder of the lower alkanol. The sparging of the lower alkanol/inorganic acid mixture is continued until all the β-naphthol initial reactant is converted to 2-alkoxy naphthalene or byproduct.

The process of the present invention is generally carried out at a temperature between about 125° C. and 175° C. at atmospheric pressure.

It has been found, in the implementation of the process of this invention that the fastest reaction rate occurs at the fastest feed rate of the mixture of lower alkanol and acid. Also increasing the acid concentration in the mixture appears to increase the overall reaction rate, other conditions being constant. At a constant alkanol/acid feed rate and acid level, an increase in the reaction temperature has been observed to have minimal effect on the reaction rate.

Further, the process of the present invention advantageously provides a quantitative conversion of the β-naphthol initial charge. Moreover, the entire working capacity of the reactor can be filled with β-naphthol since the volumes of the inorganic acid and of the lower alkanol that react are negligible and the excess lower alkanol does not remain in the reactor.

With the process of the present invention extremely rapid reactions are obtainable due, it is believed, at least in part, to the continuous removal of water of reaction.

At the end of the reaction, only crude β-alkoxy naphthalene and a very small amount of partially decomposed inorganic acid remain in the reactor. Accordingly, work up techniques to provide the desired product in a purified form are very much simplified and shortened. Thus, treatment of the reactor residue, optionally in the presence of a solvent, such as methanol, with bentonite gives a purified β-alkoxy naphthalene that is suitable for hydrogenation as is to 6-alkoxytetralin, an intermediate useful in the synthesis of certain therapeutically valuable steroids.

Alternatively, the reactor residue of crude β-alkoxy naphthalene can be distilled to give a pure grade of product, such as in the case of pure β-methoxy naphthalene which is useful as a synthetic orange blossom fragrance.

The following non-limiting examples are given to illustrate the invention. Unless otherwise specified, all parts and percentages are by weight.

EXAMPLE 1

Into a reactor fitted with a condenser there are introduced 1800 g of β-naphthol. The β-naphthol is heated to the molten state (165° C.) at which point there is introduced into the reactor, in increments over a 200 minute period a mixture of methanol and sulfuric acid. The temperature of the reaction was maintained throughout at 151°–178° C. This mixture comprised 0.4 vol. % sulfuric acid, the remainder being methanol. The methanol/sulfuric acid mixture was introduced into the reactor at a rate of 0.33 weight percent per minute based on the initial charge of β-naphthol. The reaction, which lasted 200 minutes was terminated due to the complete conversion of the β-naphthol initial charge.

Throughout the reaction, the water formed was continuously removed by distillation and eliminated from the system by means of a condenser, leading to a receiver. A small portion of the methanol charge also was removed, unreacted, from the system in this same manner thereby aiding the removal of the water of reaction.

The resulting crude β-methoxy naphthalene was subsequently removed from the flask and weighed 1890 grams.

The methanol and water which had distilled out into the receiver was allowed to evaporate. A residue of 28 grams of β-methoxynaphthalene was thereby obtained.

The total yield of β-methoxynaphthalene, 1918 grams, represented 97.1% of the theoretical yield of 1975 grams obtainable from 1800 grams of β-naphthol.

EXAMPLE 2

This example demonstrates the capability of the method to produce a β-methoxynaphthalene which can be hydrogenated to β-methoxytetralin without its being isolated in pure form prior to hydrogenation.

Into a reactor fitted with a condenser arranged for distillation, a thermometer, and an agitator there are introduced 600 grams of β-naphthol. The reactor is heated to a temperature of 125°–130° C., at which point the β-naphthol becomes molten. While maintaining the reactor contents at 125°–130° C. there is introduced under the surface of the stirred molten β-naphthol by means of a metering pump and flowmeter a steady flow of a mixture of methanol (993 ml) and concentrated sulfuric acid (7 ml). After 520 minutes there had been fed 650 ml of the methanol-sulfuric acid mixture, and gas chromatographic analysis of a sample taken from the reactor indicated no β-naphthol and a 100% conversion to β-methoxynaphthalene. The feed of methanol-sulfuric acid mixture was stopped and the reactor contents cooled down to below 60° C. The methanol and water distillate (353 grams) that had collected in the receiver was combined with the reactor contents (661 grams), new methanol (890 grams) and bentonite (30 grams). The mixture was held at reflux for two hours and then filtered to provide 1,904 grams of filtrate, which was divided into three equal portions. A portion was hydrogenated over Raney Nickel essentially according to the directions given in Stork JACS 1947, 69, 576–9 to provide a product having the composition (after methanol removal).

| | |
|---|---|
| β-methoxynaphthalene | nil |
| 2-methoxydecalin | 4.32% |
| 2-methoxytetralin | 15.14% |
| 6-methoxytetralin | 80.53% |

What is claimed is:

1. A process for the production of an alkyl aryl ether comprising incrementally reacting an acid and an alkanol with a phenol at a rate of about 0.907–0.133 weight percent per minute of the acid and alcohol based on the weight of the phenol and continuously removing water formed as a by-product of said reaction, said reaction being carried out at an elevated temperature.

2. The process of claim 1 wherein said acid is sulfuric acid, said alkanol is methanol and said phenol is naphthol.

3. The process of claim 2 wherein said naphthol is β-naphthol.

4. A process for the production of 2-methoxy naphthalene comprising incrementally reacting sulfuric acid and methanol with β-naphthol at a rate of about 0.907–0.133 weight percent per minute of the sulfuric acid and methanol based on the weight of the phenol and continuously removing water formed as a by-product of said reaction, said reaction being carried out at an elevated temperature.

5. The process of claim 4 wherein the sulfuric acid and methanol are provided in the form of a mixture thereof.

6. The process of claim 5 wherein the amount of sulfuric acid in said mixture ranges from 0.1 to 0.7 volume percent based on the volume of methanol in said mixture.

7. The process of claim 4 carried out at a temperature ranging from about 125° to 175° C.

8. A process for the production of 2-methoxy naphthalene comprising incrementally reacting a mixture of sulfuric acid and methanol with β-naphthol and continuously removing water formed as a by-product of said reaction, said methanol and sulfuric acid mixture being reacted with said β-naphthol at a rate ranging between 0.907–0.133 weight percent per minute based on the weight of β-naphthol, the concentration of said sulfuric acid in said mixture ranging from about 0.1–0.7 volume percent based on the volume of methanol in said mixture, said process being carried out at a temperature ranging between about 125°–175° C.

* * * * *